(12) United States Patent
Casula et al.

(10) Patent No.: US 9,157,997 B2
(45) Date of Patent: Oct. 13, 2015

(54) ULTRASOUND PROBING DEVICE, METHOD OF CONTROLLING TRANSDUCERS OF AN ULTRASOUND PROBE AND CORRESPONDING COMPUTER PROGRAM

(75) Inventors: Olivier Casula, Longpont sur Orge (FR); Sebastien Bey, Orsay (FR)

(73) Assignee: Commissariat á l'énergie atomique et aux énergies alternatives, Paris (FR)

( * ) Notice: Subject to any disclaimer, the term of this patent is extended or adjusted under 35 U.S.C. 154(b) by 376 days.

(21) Appl. No.: 13/878,847

(22) PCT Filed: Sep. 27, 2011

(86) PCT No.: PCT/FR2011/052259
§ 371 (c)(1),
(2), (4) Date: Apr. 11, 2013

(87) PCT Pub. No.: WO2012/049393
PCT Pub. Date: Apr. 19, 2012

(65) Prior Publication Data
US 2013/0194895 A1    Aug. 1, 2013

(30) Foreign Application Priority Data
Oct. 11, 2010 (FR) .................................... 10 58242

(51) Int. Cl.
*A61B 8/00* (2006.01)
*G01S 15/89* (2006.01)
(Continued)

(52) U.S. Cl.
CPC .......... *G01S 15/8934* (2013.01); *A61B 8/4209* (2013.01); *A61B 8/4254* (2013.01);
(Continued)

(58) Field of Classification Search
CPC .................................................. A61B 8/4466
See application file for complete search history.

(56) References Cited

U.S. PATENT DOCUMENTS 4,180,790 A * 12/1979 Thomas ............................ 367/7
4,180,792 A * 12/1979 Lederman et al. ................ 367/7
(Continued)

FOREIGN PATENT DOCUMENTS

FR         2 786 651         6/2000

OTHER PUBLICATIONS

Toullelan, G. et al., "Application of a 3D Smart Flexible Phased-Array to Piping Inspection," AIP Conference Proceedings, American Institute of Physics, vol. 975, pp. 794 to 800, (Feb. 28, 2008), XP007918186.
(Continued)

*Primary Examiner* — Ari M Diacou
(74) *Attorney, Agent, or Firm* — Oblon, McClelland, Maier & Neustadt, L.L.P.

(57) ABSTRACT

An ultrasound probing device including: a box; a locating mechanism to provide a position of the box in relation to a reference frame associated with an object to be examined; a mechanism to determine a delay law based on focusing parameters, representing a desired position of a focal point in relation to a reference frame associated with the box; a controller to provide control signals based on the delay law; transducers attached to the box, to receive control signals and, in response, to transmit ultrasonic waves in the object respectively delayed according to the delay law to focus at the focal point defined by the focusing parameters; and a mechanism updating the focusing parameters based on predefined associations between positions on a desired path of the box in relation to the reference frame associated with the object and corresponding focusing parameter values and the position of the box.

10 Claims, 5 Drawing Sheets

(51) Int. Cl.
  *G01N 29/24* (2006.01)
  *G01N 29/26* (2006.01)
  *G01N 29/265* (2006.01)
  *G01N 29/44* (2006.01)

(52) U.S. Cl.
  CPC ............. *A61B 8/4483* (2013.01); *A61B 8/4488* (2013.01); *G01N 29/24* (2013.01); *G01N 29/262* (2013.01); *G01N 29/265* (2013.01); *G01N 29/44* (2013.01); *A61B 8/4466* (2013.01)

(56) References Cited

U.S. PATENT DOCUMENTS

| | | | |
|---|---|---|---|
| 4,182,173 A * | 1/1980 | Papadofrangakis et al. | 73/861.27 |
| 4,208,916 A * | 6/1980 | Thomenius et al. | 73/626 |
| 4,211,948 A * | 7/1980 | Smith et al. | 310/322 |
| 4,217,909 A * | 8/1980 | Papadofrangakis et al. | 600/441 |
| 4,437,468 A * | 3/1984 | Sorenson et al. | 600/459 |
| 4,682,497 A * | 7/1987 | Sasaki | 73/602 |
| 5,161,413 A | 11/1992 | Junker et al. | |
| 5,212,667 A * | 5/1993 | Tomlinson et al. | 367/7 |
| 5,551,433 A * | 9/1996 | Wright et al. | 600/443 |
| 5,678,554 A * | 10/1997 | Hossack et al. | 600/459 |
| 5,680,863 A * | 10/1997 | Hossack et al. | 600/459 |
| 5,735,282 A * | 4/1998 | Hossack | 600/458 |
| 5,913,825 A * | 6/1999 | Watanabe et al. | 600/459 |
| 6,042,556 A * | 3/2000 | Beach et al. | 601/3 |
| 6,424,597 B1 * | 7/2002 | Bolomey et al. | 367/138 |
| 6,582,369 B1 * | 6/2003 | Huang et al. | 600/447 |
| 8,402,830 B2 * | 3/2013 | Kleinert et al. | 73/629 |
| 8,453,509 B2 * | 6/2013 | Oberdorfer et al. | 73/632 |
| 8,714,018 B2 * | 5/2014 | Oberdoerfer et al. | 73/632 |
| 2002/0016546 A1 * | 2/2002 | Cerofolini | 600/443 |
| 2007/0167800 A1 * | 7/2007 | Casula et al. | 600/459 |
| 2010/0030076 A1 * | 2/2010 | Vortman et al. | 600/439 |
| 2011/0016978 A1 * | 1/2011 | Kleinert et al. | 73/629 |
| 2011/0016979 A1 * | 1/2011 | Oberdorfer et al. | 73/632 |

OTHER PUBLICATIONS

Casula, O. et al., "Ultrasonic Nondestructive Testing of Complex Components With Flexible Phased-Array Transducers," Proceedings of the 10th European Conference on Non-Destructive Testing, Total 9 pages, (Jun. 11, 2010), XP007918185.

International Search Report Issued Dec. 16, 2011 in PCT/FR11/52259 Filed Sep. 27, 2011.

* cited by examiner

ULTRASOUND PROBING DEVICE, METHOD OF CONTROLLING TRANSDUCERS OF AN ULTRASOUND PROBE AND CORRESPONDING COMPUTER PROGRAM

BACKGROUND OF THE INVENTION

1. Field of the Invention

The present invention relates to an ultrasound probing device, a method for controlling transducers of an ultrasound probe and a corresponding computer program.

The invention particularly applies to the field of medical imaging, and to non-destructive testing of mechanical parts, particularly parts having a complex shape.

2. Description of the Related Art

The following terminology will be used hereinafter in the description and in the claims.

An ultrasonic, or ultrasound, wave is a mechanical wave having frequencies greater than 20,000 Hertz propagating in a solid, liquid or gas medium.

The terms "position or orientation of an element X in relation to an element Y" signify "position or orientation of a reference frame associated with the element X in relation to a reference frame associated with the element Y".

The French patent published under the number FR 2 786 651 describes an ultrasound probing device comprising a box, locating means designed to provide a position $P_{B/O}$ of the box in relation to a reference frame associated with an object to be examined, means for determining a delay law on the basis of focusing parameters, referenced $P_{F/B}$, representing a desired position of a focal point in relation to a reference frame associated with the box, control means designed to provide control signals on the basis of the delay law, and transducers attached to the box, designed to receive control signals and, in response, to transmit ultrasonic waves in the object which are delayed with respect to each other according to the delay law such that they focus at the focal point defined by the focusing parameters $P_{F/B}$.

In this document, the transducers are attached in a movable manner to the box so as to be able to follow the geometry of the surface of the object to be examined. Means for determining the positions of the transducers at all times and for providing these positions to the means for determining the delay law are thus provided. In this way, the means for determining the delay law can account for the positions of the movable transducers to correct the delay law applied and retain the desired position of the focal point in relation to the box.

However, this flexibility has its limitations since a single desired position of the focal point in relation to the box, predetermined for the entire period of probing of the objects and directly integrated in the formulas applied by the means for determining the delay law, is envisaged.

It may thus be sought to provide an ultrasound probing device offering more flexibility in the use thereof, particularly for example by enabling complex focal point paths during the probing of the object.

SUMMARY OF THE INVENTION

The invention thus relates to an ultrasound probing device comprising a box, locating means designed to provide a position $P_{B/O}$ of the box in relation to a reference frame associated with an object to be examined, means for determining a delay law on the basis of focusing parameters, referenced $P_{F/B}$, representing a desired position of a focal point in relation to a reference frame associated with the box, control means designed to provide control signals on the basis of the delay law, and transducers attached to the box, designed to receive control signals and, in response, to transmit ultrasonic waves in the object which are delayed with respect to each other according to the delay law such that they focus at the focal point defined by the focusing parameters $P_{F/B}$, and means for updating the focusing parameters $P_{F/B}$ based on predefined associations between positions on a desired path of the box in relation to the reference frame associated with the object and the corresponding focusing parameter values and the position $P_{B/O}$ of the box.

In this way, with the invention, it is possible to envisage modifications of the focusing parameters, i.e. of the desired position of the focal point in relation to the box, in the course of the path followed by the box and the transducers of the probing device. The invention thus makes it possible to obtain more freedom in the path followed by the focal point in the object to be examined. For example, it is possible to modify the depth of the focal point (distance between the surface of the object where the transducers are applied and the focal point) according to the path followed by the box and the transducers so as to follow an irregular base of an object from a flat opposite face.

Optionally, the means for locating the box comprise a sensor designed to measure the position $P_{B/O}$ of the box.

Also optionally, the updating means comprise selection means designed to provide a focusing parameter value associated, by means of the predefined associations, with at least one position of the desired path, on the basis of the position $P_{B/O}$ of the box.

Also optionally, the updating means are designed to update the focusing parameters $P_{F/B}$ to the focusing parameter value provided by the selection means.

Also optionally, the updating means further comprise:
adjustment means designed to determine an adjusted position of the box in relation to the reference frame associated with the object on the desired path on the basis of the position $P_{B/O}$ of the box, this adjusted position being referenced $P_{\underline{B}/O}$, and/or an adjusted orientation of the box on a desired orientation of the box on the basis of the orientation $O_{B/O}$ of the box, this adjusted orientation being referenced $O_{\underline{B}/O}$,
means for determining deviations designed to determine a deviation in position, referenced $P_{B/\underline{B}}$, between the position $P_{B/O}$ of the box and the adjusted position $P_{\underline{B}/O}$, and/or a deviation in orientation, referenced $O_{B/\underline{B}}$, between the orientation $O_{B/O}$ of the box and the adjusted orientation $O_{\underline{B}/O}$,
correction means designed to correct the focusing parameter value provided by the selection means on the basis of the deviation in position $P_{B/\underline{B}}$ and/or the deviation in orientation $O_{B/\underline{B}}$,
and the updating means are designed to update the focusing parameters $P_{F/B}$ to the corrected focusing parameter value provided by the correction means.

Also optionally, the desired path comprising path segments $S^{(i)}$, the predefined associations associate reference focusing parameter values $P_{ref}^{(i)}{}_{F/B}$ respectively with each path segment $S^{(i)}$, and the selection means are designed to select one of the path segments $S^{(i)}$ on the basis of the position $P_{B/O}$ of the box and to provide the reference value $P_{ref}^{(i)}{}_{F/B}$ associated with the selected path segment $S^{(i)}$.

Also optionally, the predefined associations comprise parameters of an adjustment operation providing a focusing parameter value on the basis of a position on the desired path and the selection means comprise means designed to calculate, using the adjustment operation parameters, the value of the focusing parameters on the basis of a position on the desired path determined on the basis of the position $P_{B/O}$ of the box.

Also optionally, the transducers are attached in a movable manner to the box, the device comprises means for locating the transducers designed to determine positions $P_{t/B}$ of the transducers in relation to a reference frame associated with the box, and the means for determining the delay law are further designed to determine the delay law on the basis of these positions $P_{t/B}$ of the transducers.

The invention also relates to a method for controlling transducers of an ultrasound probe, comprising the following step:
receiving a position $P_{B/O}$ of a box of the probe in relation to a reference frame associated with an object to be examined, the transducers being attached to this box,
determining a delay law on the basis of focusing parameters, referenced $P_{F/B}$, representing a desired position of a focal point in relation to a reference frame associated with the box,
providing control signals to the transducers on the basis of the delay law, and
updating the focusing parameters $P_{F/B}$, on the basis of predefined associations between positions on a desired path of the box in relation to the reference frame associated with the object and the corresponding focusing parameter values and the position $P_{B/O}$ of the box.

The invention also relates to a computer program suitable for being downloaded from a communication network and/or saved on a medium suitable for being read by a computer and/or executed by a processor, comprising instructions for the implementation of a method for controlling transducers of an ultrasound probe according to the invention, when said program is executed by a computer.

DESCRIPTION OF THE DRAWINGS

The invention will be understood more clearly using the description hereinafter, given merely as an example and referring to the appended figures wherein.

DETAILED DESCRIPTION OF THE INVENTION

First Embodiment

Figure 1:
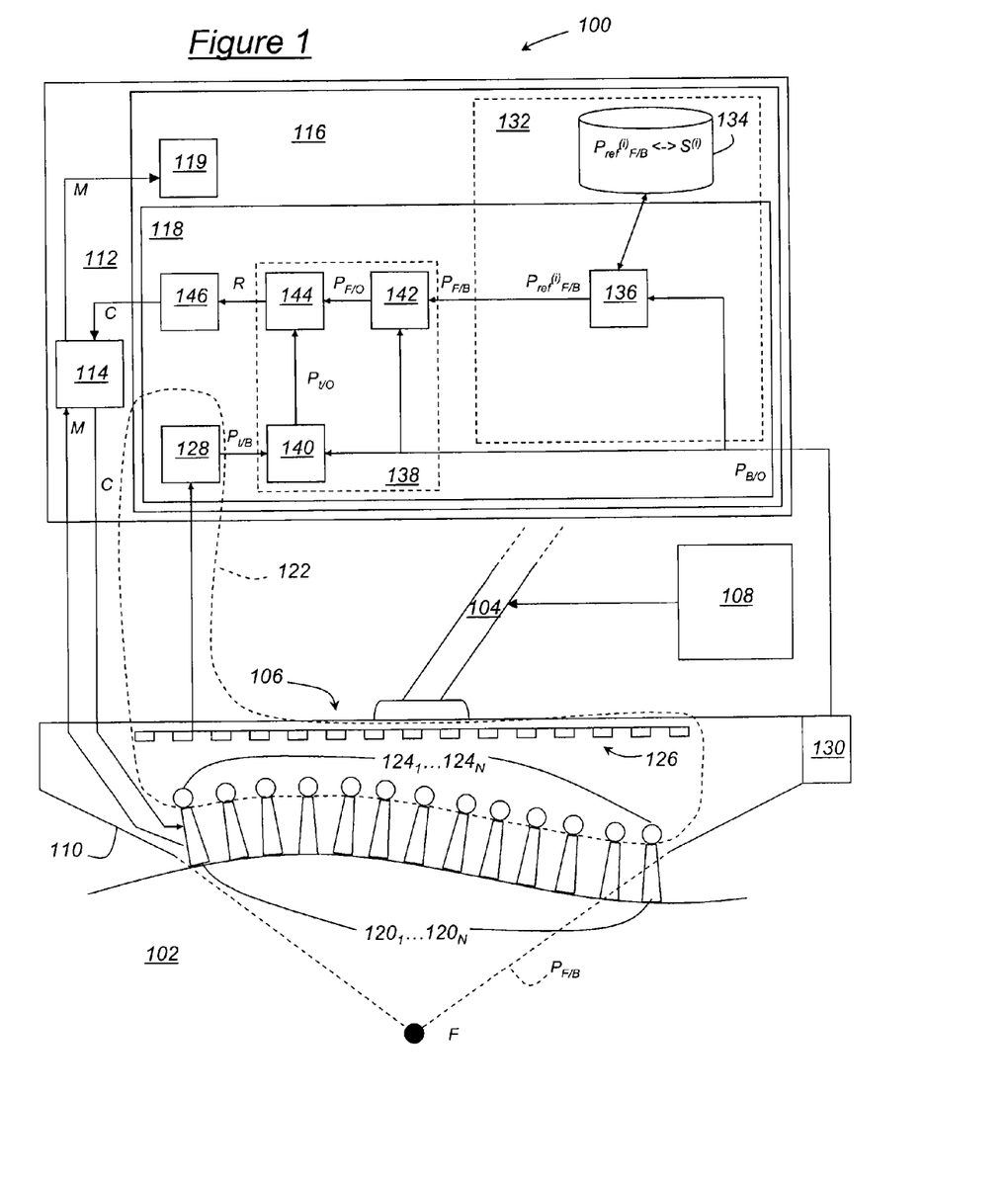
FIG. 1 schematically represents the general structure of a device for probing an object comprising an ultrasound probe, according to a first embodiment of the invention.

With reference to FIG. 1, a device 100 for probing an object 102 according to a first embodiment of the invention comprises an arm 104, which is hinged in the example described, an ultrasound probe 106 attached to the hinged arm 104 and means 108 for controlling the hinged arm 104 designed to control the hinged arm 104 so that the arm moves the probe 106 over a surface of the object 102. The means 108 for controlling the hinged arm are generally based on a predefined desired path of the probe 106 in relation to the object 102.

The object 102 is, for example, a mechanical part to be examined by non-destructive testing or, in a medical context, a part of the human body to be examined non-invasively.

Furthermore, the probing device 100 comprises an electronic circuit 112, for example that of a computer. This electronic circuit 112 is connected to the probe 106. It has a central processing unit 114, such as a microprocessor, and a memory 116 wherein a computer program 118 for controlling the probe 106 and a computer program 119 for processing signals are saved. These programs 118 and 119 comprise instructions to be executed by the central processing unit 114 to carry out the functions defined by these instructions.

The probe 106 firstly comprises a box 110, i.e. a non-deformable structural element which serves as a reference frame for the probe 106.

The probe 106 further comprises transducers $120_1 \ldots 120_N$ attached to the box 110 and designed to transmit ultrasonic waves in the object 102 in response to control signals C provided by the electronic circuit 112. The transducers $120_1 \ldots 120_N$ are further designed to detect echoes of the ultrasonic waves reflected on and in the object 102 and to provide measurement signals M corresponding to these echoes, these measurement signals M being transmitted to the electronic circuit 112. More specifically, the central processing unit 114 is designed to transmit, to the probe 106, the control signals C and to receive, from the probe 106, the measurement signals M.

In the probe 106 in FIG. 1, the transducers $120_1 \ldots 120_N$ are attached in a movable manner to the box 110, such that they are suitable for following the surface of the object 102 whereon they are moving, even if said surface is not plane, as illustrated in FIG. 1.

Furthermore, the probing device 100 comprises means 122 for locating the transducers $120_1 \ldots 120_N$ designed to determine the positions of the transducers $120_1 \ldots 120_N$ in relation to the box 110, these positions being referenced $P_{t/B}$.

In the probing device 100 in FIG. 1, the means 122 for locating the transducers $120_1 \ldots 120_N$ comprise transmitters $124_1 \ldots 124_N$ designed to transmit electromagnetic waves for example. Each transmitter $124_1 \ldots 124_N$ is attached to a respective transducer $120_1 \ldots 120_N$. The means 122 for locating the transducers $120_1 \ldots 120_N$ further comprise receivers 126 attached to the box 110 and designed to detect the waves transmitted by the transmitters $124_1 \ldots 124_N$. The means 122 for locating the transducers $120_1 \ldots 120_N$ further comprise instructions 128 of the computer program 118 for determining the positions $P_{t/B}$ of the transducers $120_1 \ldots 120_N$ on the basis of the detections of receivers 126, for example by triangulation. The locating means 122 are for example such as those described in detail in the patent FR 2 786 651.

Alternatively, other means for locating transducers may be used, for example those also envisaged in the patent FR 2 786 651.

The probing device 100 further comprises means 130 for locating the box 110 designed to provide a position of the box 110 in relation to the object 102, referenced $P_{B/O}$. In the probing device 100 in FIG. 1, the locating means 130 comprise a position sensor attached to the box 110 and designed to determine the actual position of the box 110 in relation to the object 102. According to one alternative embodiment wherein the probing device 100 comprises a handle (not shown) attached to the box 110 instead of the end of the hinged arm 104, the sensor 130 may be attached to the handle.

Alternatively, the means 130 for locating the box 110 could be a database wherein the desired path of the box 110 in relation to the object 102 is saved, for example the path used by the means 108 for controlling the hinged arm 104. In this case, the position $P_{B/O}$ of the box 110 would be the desired position of the box 110.

The probing device 100 further comprises means 132 for updating focusing parameters, referenced $P_{F/B}$, representing a desired position of a focal point F in relation to the box 110. The updating means 132 are designed to update the focusing parameters $P_{F/B}$ on the basis of predefined associations between positions on the desired path of the box 110 and corresponding values of the focusing parameters, and the position $P_{B/O}$ of the box 110.

In the probing device in FIG. 1, the desired path comprises linear path segments $S^{(i)}$, for example arranged end to end, and the predefined associations associate reference values $P_{ref}^{(i)}{}_{F/B}$ of the focusing parameters with respectively each path segment $S^{(i)}$.

For this purpose, the updating means 132 firstly comprise a database 134 saved in the memory 116 and comprising predefined associations. The updating means 132 further comprise instructions, referred to as selection instructions 136, for providing a focusing parameter value associated, by means of the predefined associations, with at least one position on the desired path, on the basis of the position $P_{B/O}$ of the box 110.

More specifically, in the probing device in FIG. 1, the selection instructions 136 are designed to select, in the database 134 one of the desired path segments $S^{(i)}$ on the basis of the position $P_{B/O}$ of the box 110, and to provide the reference value $P_{ref}^{(i)}{}_{F/B}$ associated with the selected path segment $S^{(i)}$. For this purpose, the selection instructions 136 are designed to determine whether the position $P_{B/O}$ of the box 110 is situated in a sphere of uncertainty about one of the path segments $S^{(i)}$, i.e. in the vicinity of the path segment $S^{(i)}$ according to a predefined proximity rule and to select the path segment $S^{(i)}$ and provide the associated reference value $P_{ref}^{(i)}{}_{F/B}$.

Furthermore, the updating means 132 are designed to update the focusing parameters $P_{F/B}$ on the basis of the focusing parameter values provided by the selection means 136. Again in the probing device 100 in FIG. 1, the updating means 132 are thus designed to update the focusing parameters $P_{F/B}$ to the reference value $P_{ref}^{(i)}{}_{F/B}$ provided by the selection means 136.

The program 118 further comprises instructions 138 for determining a delay law R on the basis of the focusing parameters $P_{F/B}$ provided by the updating means 132 and the positions of the transducers in relation to the box $P_{t/B}$.

In the probing device 100 in FIG. 1, the instructions 138 for determining the delay law firstly comprise instructions 140 for determining the positions, referenced $P_{t/O}$, of the transducers in relation to the object 102 on the basis of the positions $P_{t/B}$ of the transducers in relation to the box 110 and the position $P_{B/O}$ of the box 110 in relation to the object 102: this merely consists of a change of reference. The instructions 138 for determining the delay law R further comprise instructions 142 for determining the focusing parameters, referenced $P_{F/O}$, in relation to the object 102 (the focusing parameters $P_{F/O}$ thus representing the desired position of the focal point F in relation to the object 102) on the basis of the focusing parameters $P_{F/B}$ and the position $P_{B/O}$ of the box 110. This operation thus also merely consists of a change of reference in a manner known per se. The instructions 138 for determining the delay law R further comprise instructions 144 for determining the delay law R on the basis of the focusing parameters $P_{B/O}$ in relation to the object 102 and the positions $P_{t/O}$ of the transducers $120_1 \ldots 120_N$ in relation to the object 102. This operation particularly comprises the calculation of paths between the transducers $120_1 \ldots 120_N$ and the desired position of the focal point F, in a manner known per se.

Finally, the program 118 comprises control instructions 146 for determining the control signals C intended for the transducers $120_1 \ldots 120_N$, on the basis of the delay law R. More specifically, the instructions 146 are designed such that the control signals C have delays with respect to each other defined par the delay law R. In this way, by means of the delays in the control signals C, the ultrasonic waves can focus at the focal point F positioned as desired.

Figures 2, 5:
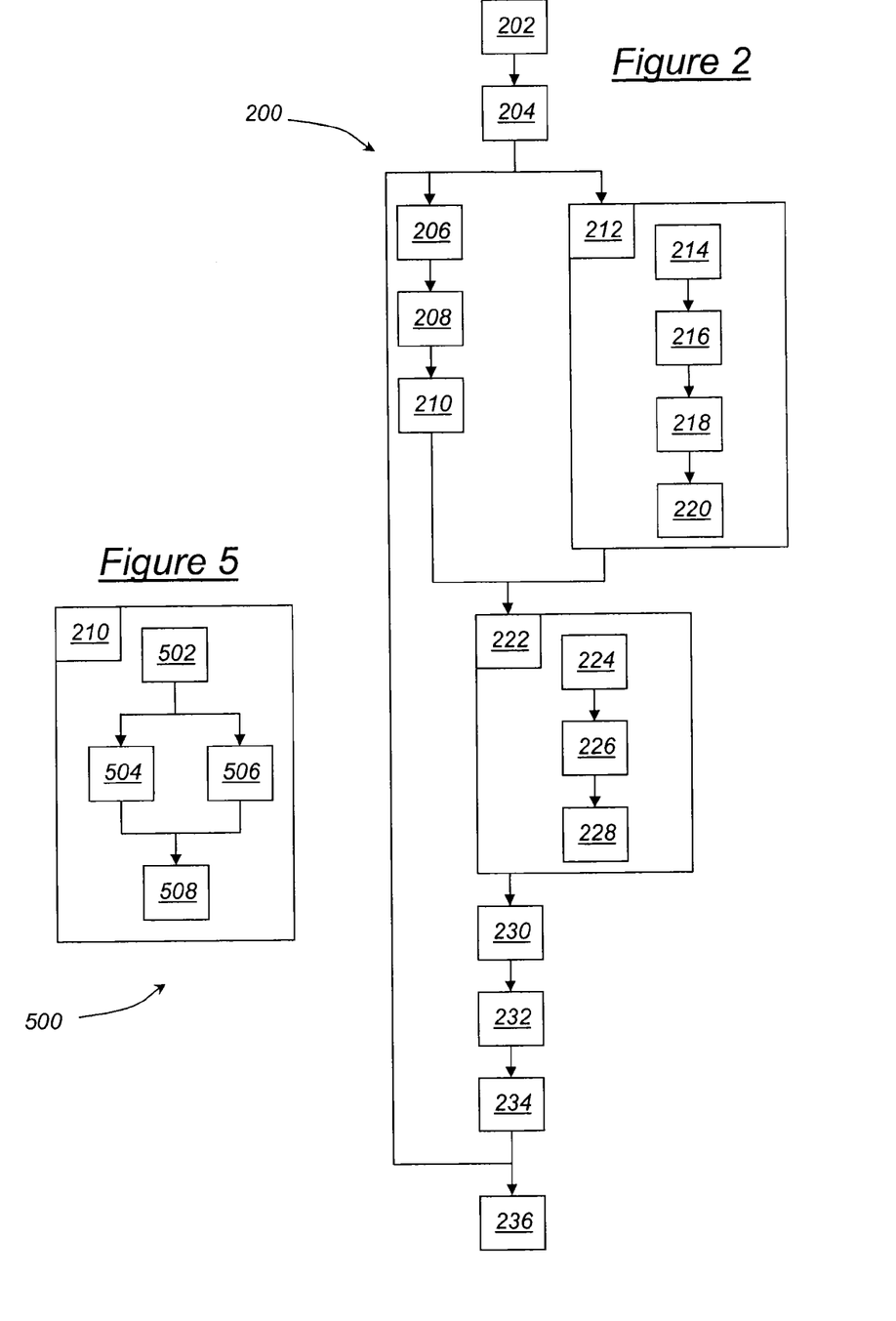
FIG. 2 illustrates the successive steps of a probing method implemented using the device in FIG. 1.
FIG. 5 illustrates the successive steps of a probing method implemented using the device in FIG. 4.

With reference to FIG. 2, a method for probing 200 the object 102 using the probing device 100 will now be described.

During a step 202, an operator configures the control means 108 of the hinged arm 104 so that the arm can move the probe 106 along the desired path in contact with the object 102.

During a step 204, the operator defines the associations between positions on the desired path of the box 110 and corresponding focusing parameter values. In the example described, the operator saves, in the database 134, the associations between the path segments $S^{(i)}$ of the desired path and the reference values $P_{ref}^{(i)}{}_{F/B}$ of the focusing parameters.

It should be noted that steps 202 and 204 are preferably carried out before the probing device 100 starts the actual probing of the object 102. Subsequently, the probe 106 moves in relation to the object 102.

During a step 206, the locating means 130 determine the position $P_{B/O}$ of the box 110.

During a step 208, the central processing unit 114 executing the control program 118 receives the position $P_{B/O}$ of the box 110 from the locating means 130.

During a step 210, the updating means 132 update the focusing parameters $P_{F/B}$ on the basis of the position $P_{B/O}$ of the box 110. More specifically, the central processing unit 114 executing the instructions 136 provides, on the basis of the position $P_{B/O}$ of the box 110, a focusing parameter value associated, by means of the predefined associations, with at least one position on the desired path. The focusing parameters $P_{F/B}$ are updated to this value. In the example described, the central processing unit 114 executing the selection instructions 136 selects, in the database 134, one of the path segments $S^{(i)}$ on the basis of the position $P_{B/O}$ of the box 110, and provides the associated reference value $P_{ref}^{(i)}{}_{F/B}$ in the database 134.

During a step 212, the means 122 for locating the transducers $120_1 \ldots 120_N$ determine the positions $P_{t/B}$ of the transducers $120_1 \ldots 120_N$. More specifically, this step 212 comprises the following steps 214 to 220.

During a step 214, the transmitters $124_1 \ldots 124_N$ transmit locating waves.

During a step 216, the receivers 126 detect the locating waves.

During a step 218, the central processing unit 114 executing the program 118 receives the detections from the receivers 126.

During a step 220, the central processing unit 114 executing the instructions 128 determines the positions $P_{t/B}$ of the transducers $120_1 \ldots 120_N$ on the basis of the detections of the receivers 126.

During a step 222, the central processing unit 114 executing the instructions 138 determines the delay law R on the basis of the focusing parameters $P_{F/B}$ updated by the updating means 132 and the positions $P_{t/B}$ of the transducers $120_1 \ldots 120_N$. More specifically, the step 222 comprises the following steps 224 to 228.

During a step 224, the central processing unit 114 executing the instructions 140 determines the positions $P_{t/O}$ of the transducers $120_1 \ldots 120_N$ in relation to the object 102 on the basis of the positions $P_{t/B}$ of the transducers $120_1 \ldots 120_N$ and the position $P_{B/O}$ of the box 110.

During a step 226, the central processing unit 114 executing the instructions 142 determines the focusing parameters $P_{F/O}$ in relation to the object 102 on the basis of the focusing parameters $P_{F/B}$ and the position $P_{B/O}$ of the box 110.

During a step 228, the central processing unit 114 executing the instructions 144 determines the delay law R on the basis of the focusing parameters $P_{F/O}$ in relation to the object 102 and the positions $P_{t/O}$ of the transducers $120_1 \ldots 120_N$ in relation to the object 102.

During a step 230, the central processing unit 114 executing the instructions 146 triggers the provision to the transducers $120_1 \ldots 120_N$, by the electronic circuit 112, of control signals C having delays with respect to each other defined by the delay law R.

During a step 232, the transducers $120_1 \ldots 120_N$, in response to the control signals C, transmit ultrasonic waves into the object 102, which focus at a focal point F having the desired position in relation to the box 110, by means of the delays of the control signals C with respect to each other.

During a step 234, the transducers $120_1 \ldots 120_N$ receive the echoes of the ultrasonic waves reflected on and in the object 102, and provide the processing program 119 with the corresponding measurement signals M.

The method 200 then returns to steps 206 and 212.

In parallel with steps 206 to 212, or thereafter, after the probe 106 has completed the planned path, during a step 236, the central processing unit 114 executing the instructions of the processing program 119 processes the measurement signals M, for example in order to detect structural defects in the object 102, displaying the processing results on a screen.

Figure 3:
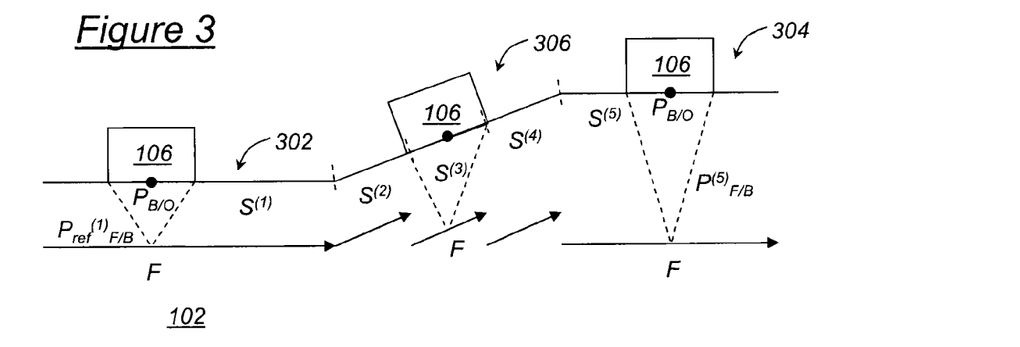
FIG. 3 illustrates a path of the probe in FIG. 1 on the object to be examined, and the movement of a focal point of the probe in the object, FIG. 4 schematically represents the general structure of a device for probing an object comprising an ultrasound probe, according to a second embodiment of the invention.

With reference to FIG. 3, an example of use of the device 100 in FIG. 1 will now be described.

The object 102 comprises a face having, in the plane of FIG. 3, two horizontal parts 302, 304 and one oblique part 306 connecting the two horizontal parts 302, 304.

The desired path of the probe, corresponding to the known shape of the face of the object 102, comprises five path segments $S^{(1)} \ldots S^{(5)}$, each associated with a respective reference value $P^{(1)}{}_{F/B} \ldots P^{(5)}{}_{F/B}$ of focusing parameters. These associations are saved in the database 134.

The first path segment $S^{(1)}$ covers the horizontal part 302, such that the focal point F moves parallel with this horizontal part 302, at a depth of the horizontal part 302 defined by the first reference value $P^{(1)}{}_{F/B}$ associated with the first path segment $S^{(1)}$.

The next three path segments $S^{(2)} \ldots S^{(4)}$ cover the oblique part 306. The focal point F moves parallel with the oblique part 306 but is returned, at the start of each path segment $S^{(2)} \ldots S^{(4)}$, in line with the movement thereof for the first straight part 302. This is obtained by selecting reference values $P^{(2)}{}_{F/B} \ldots P^{(4)}{}_{F/B}$ defining positions of the focal point F at increasing depths and with a suitable angle for the oblique part 306.

The fifth path segment $S^{(5)}$ covers the second straight part 304. The focal point F moves parallel with the horizontal part 304, at a depth of the horizontal part 304 defined by the fifth reference value $P^{(5)}{}_{F/B}$, such that the focal point F moves in line with the movement thereof for the first horizontal part 302.

In this way, the focal point F moves relatively linearly when the probe 106 moves on the face of the object 102, despite the fact that the surface of the object 102 is not a solely horizontal line. According to this embodiment, it is understood that the linearity of the movement of the focal point F in the object 102 is enhanced by increasing the number of segments associated with focusing parameters in the parts of the desired path which are not parallel with the desired movement of the focal point F. In particular, in the example in FIG. 3, the greater the number of segments covering the oblique part 306 (in this case three), the closer the path actually followed by the focal point F in the object 102 to the ideally desired horizontal rectilinear path.

Second Embodiment

Figure 4:
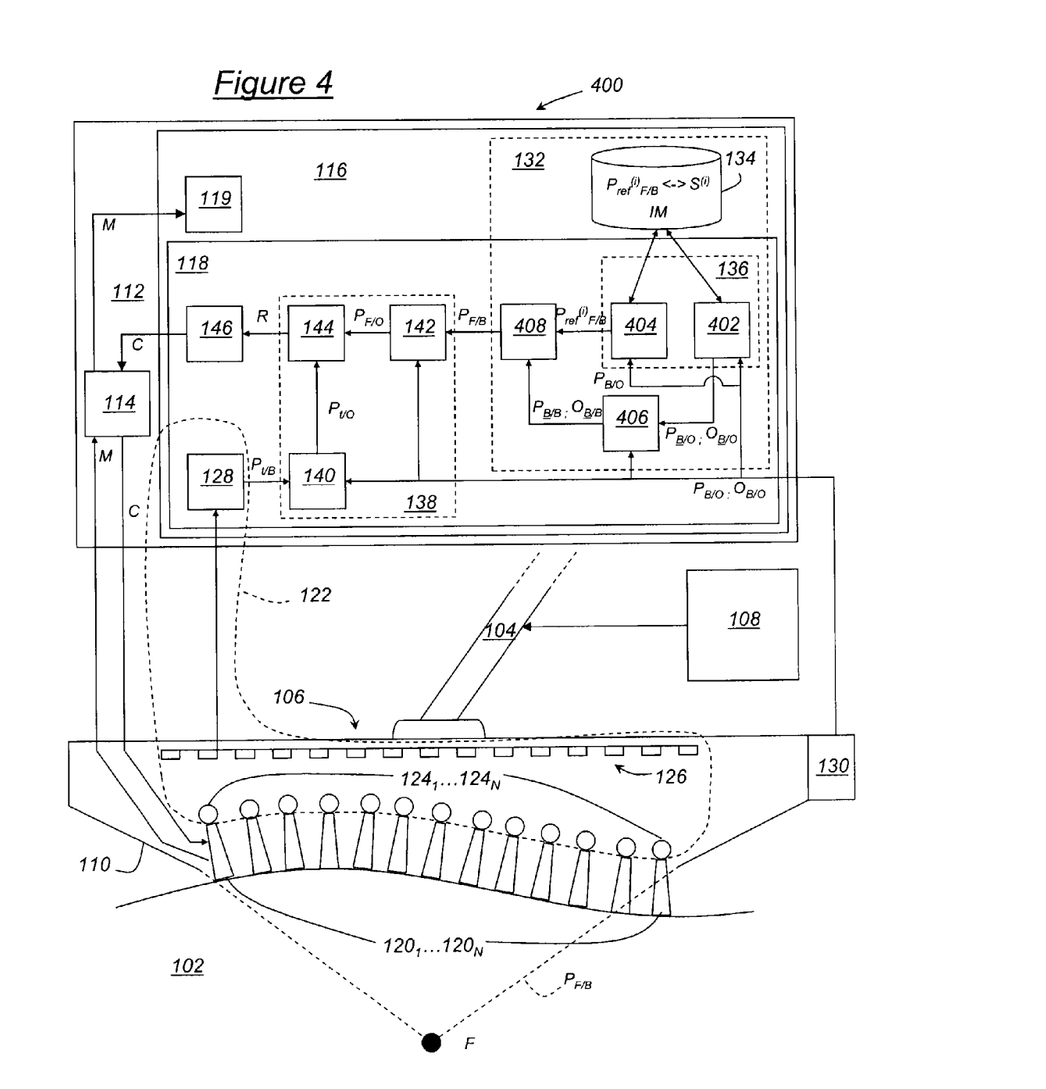

With reference to FIG. 4, a probing device 400 according to a second embodiment of the invention comprises the same elements as the device in FIG. 1, for which the same references are used, except for the elements to be described hereinafter. According to this second embodiment, the probing device 400 is designed to account for a deviation between an actual position and/or orientation of the box 110, and a desired position and/or orientation on the desired path, in the update of the focusing parameters $P_{F/B}$.

In this way, in the probing device 400 in FIG. 4, the locating means 130 are not only designed to provide a position $P_{B/O}$ of the box in relation to the object 102, but further designed to provide an orientation $O_{B/O}$ of the box 110 in relation to the object 102.

Moreover, the updating means 132 still comprise the database 134, but the database now further comprises desired movement data, referenced IM, defining a desired movement of the box 110 in relation to the object 102. The desired movement data IM particularly comprise desired path data defining the desired path of the box 110 in relation to the object 102, and desired orientation data defining the desired orientation of the box 110 in relation to the object 102 along the desired path. In the device in FIG. 4, the desired path data comprise path segments $S^{(i)}$ of the predefined associations.

The selection instructions 136 further comprise instructions 402, referred to as adjustment instructions 402, for determining an adjusted position of the box 110 in relation to the object 102 on the desired path, this adjusted position being referenced $P_{B/O}$. The adjusted position $P_{B/O}$ is determined on the basis of the position $P_{B/O}$ of the box 110, provided by locating means 130, and the desired path data from the database 134. For example, the adjusted position is the point of the desired path closest to the position of the box in relation to the object $P_{B/O}$. The adjustment instructions 402 are further designed to determine an adjusted orientation, referenced $O_{B/O}$, of the box 110 on the desired orientation of the box 110, on the basis of the orientation $O_{B/O}$ of the box 110 and the desired orientation data from the database 134.

In the probing device 400 in FIG. 4, the selection instructions 136 further comprise instructions, referred to as selection instructions 404, for selecting one of the path segments $S^{(i)}$ on the basis of the non-adjusted position $P_{B/O}$ and the desired path data from the database 134. Moreover, the selection instructions 136 are designed to provide the reference value $P_{ref}{}^{(i)}{}_{F/B}$ associated with the selected path segment $S^{(i)}$.

The updating means 132 further comprise instructions from the control program 118, referred to as deviation determination instructions 406, for determining the deviation in position $P_{\underline{B}/B}$ between the position $P_{B/O}$ of the box 110 and the adjusted position $P_{\underline{B}/O}$ of the box 110, and the deviation in orientation, referenced $O_{\underline{B}/B}$, between the orientation $O_{B/O}$ of the box 110 and the adjusted orientation $O_{\underline{B}/O}$ thereof.

The updating means 132 further comprise instructions from the control program 118, referred to as correction instructions 408, for correcting the focusing parameter value provided by the selection instructions 136 on the basis of the deviation in position $P_{\underline{B}/B}$ and the deviation in orientation $O_{\underline{B}/B}$. In the example described, the focusing parameter value provided by the selection instructions 136 is, as explained above, one of the reference values $P_{ref}^{(i)}{}_{F/B}$ of the database 134.

The updating means 132 are thus designed to update the focusing parameters $P_{F/B}$ to the focusing parameter value corrected by the correction instructions 408.

The focusing parameters $P_{F/B}$ updated in this way are suitable for positioning the focal point F at the same point as if the box 110 had the desired position and desired orientation thereof.

With reference to FIG. 5, a method for probing 500 the object 102 using the probing device 400 comprises the same steps as the method 200 in FIG. 2, except for the step 210 now comprising the following steps for updating the focusing parameters $P_{F/B}$ according to the position $P_{B/O}$ of the box 110 and the orientation $O_{B/O}$ thereof.

During a step 502, the central processing unit 114 executing the instructions 402 determines the adjusted position $P_{\underline{B}/O}$ and the adjusted orientation $O_{\underline{B}/O}$ of the box 110, on the basis of the desired movement data IM from the database 134, the position $P_{B/O}$ of the box 110 and the orientation $O_{B/O}$ thereof.

During a step 504, the central processing unit 114 executing the instructions 404 selects, in the database 134, a path segment $S^{(i)}$ on the basis of the non-adjusted position $P_{B/O}$ of the box 110, and provides the reference value $P_{ref}^{(i)}{}_{F/B}$ of the focusing parameters associated with this path segment $S^{(i)}$.

In parallel with the step 504, during a step 506, the central processing unit 114 executing the instructions 406 determines the deviation in position $P_{\underline{B}/B}$ and the deviation in orientation $O_{\underline{B}/B}$.

During a step 506, the central processing unit 114 executing the instructions 408 corrects the reference value of the focusing parameters on the basis of the deviations in position $P_{\underline{B}/B}$ and orientation $O_{\underline{B}/B}$. This corrected value thus constitutes the updated focusing parameters $P_{F/B}$.

Figure 6:
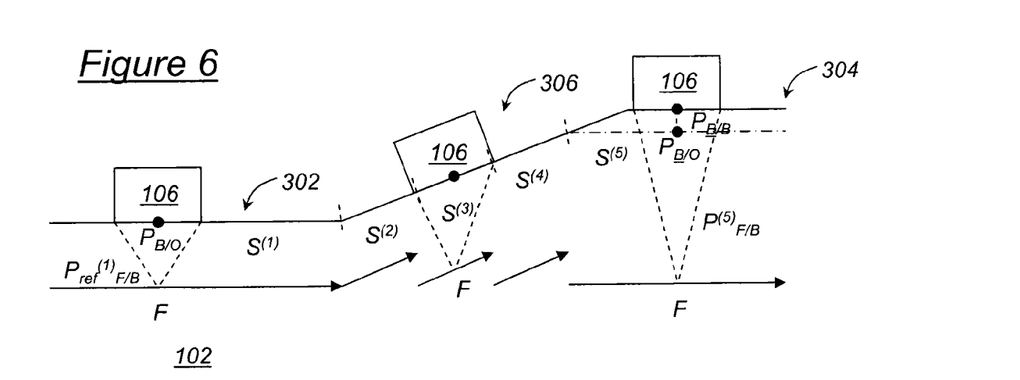
FIG. 6 illustrates a path of the probe in FIG. 4 on the object to be examined, and the movement of a focal point of the probe in the object, FIG. 7 schematically represents the general structure of a device for probing an object comprising an ultrasound probe, according to a third embodiment of the invention.

With reference to FIG. 6, a similar example to that in FIG. 3 will now be described, to illustrate the correction of a positioning error. Those skilled in the art could readily adapt this example to an orientation correction.

The probe 106 is intended to follow the desired path consisting of the five path segments $S^{(1)} \ldots S^{(5)}$ (where the path segment $S^{(5)}$ is represented as a mixed dashed line in this figure). On the part 304 of the object 102, the probe 106 has deviated from the desired path by a deviation represented by $P_{\underline{B}/B}$ given that the actual face of the object 102 whereon it is moving does not precisely match the desired path saved in the database 134.

This deviation may be due to the fact that the parts allow machining tolerances which may be greater than the precisions required for probing or a part positioning error. Furthermore, the probe 106 is liable not to follow the desired surface exactly. Failing correction, these deviations would result in poor focusing of the ultrasonic wave beam in the desired area since the calculated delays would not be adapted to the desired focal points.

However, in the present invention, by means of the deviation correction provided in the instructions 138, the focal point F is not affected by the positioning error of the probe 106. This correction solution is an advantageous substitute for a mechanical correction, on the hinged arm 104 for example.

Third Embodiment

Figure 7:
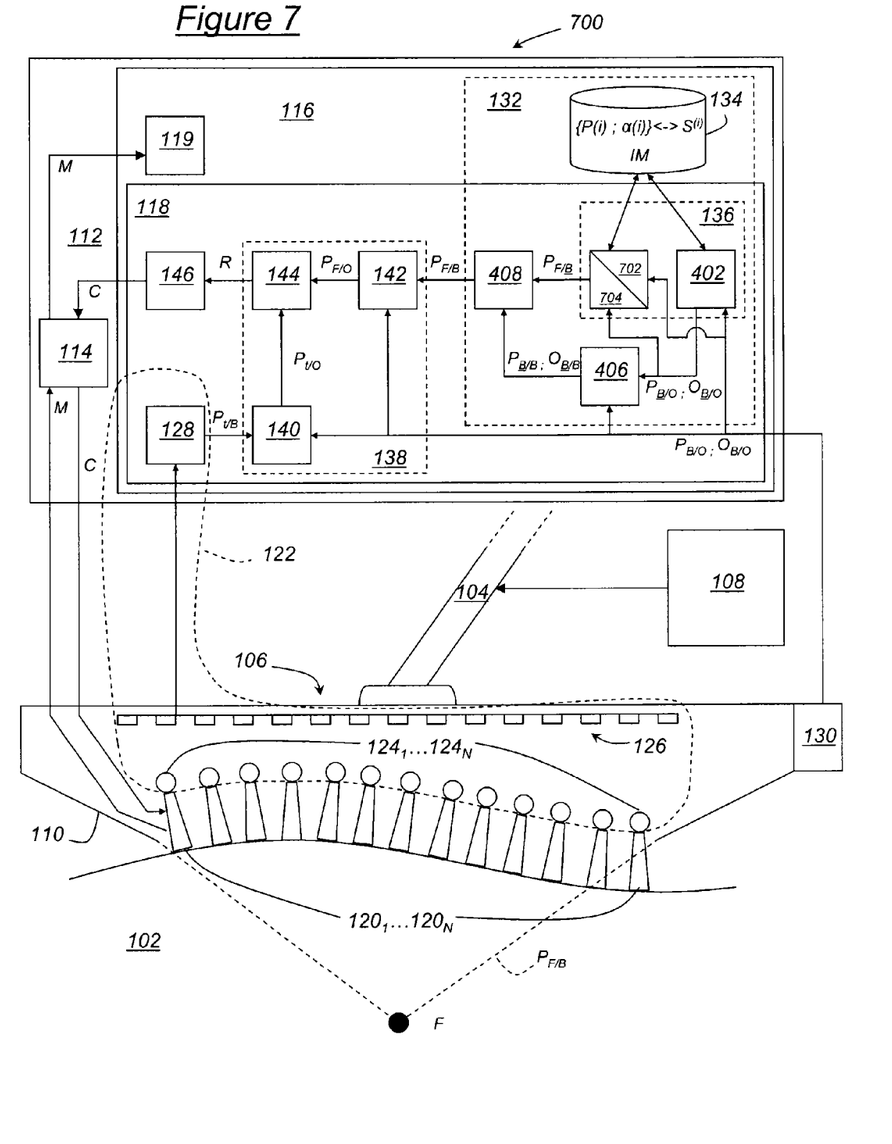
Figure 8:
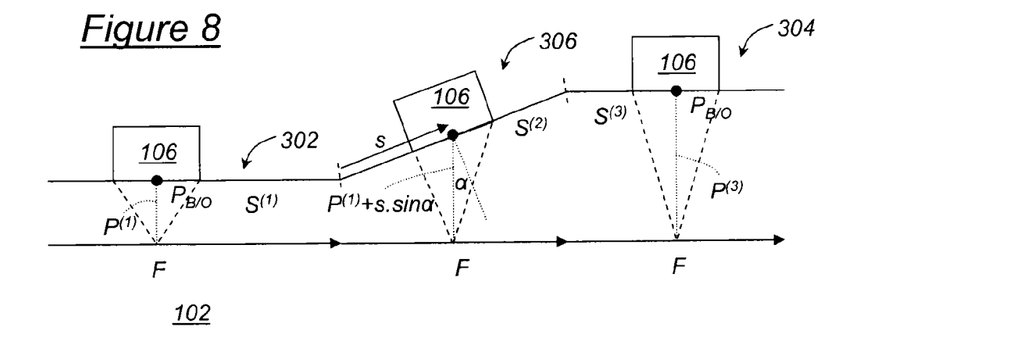
FIG. 8 illustrates a path of the probe in FIG. 7 on the object to be examined, and the movement of a focal point of the probe in the object.

With reference to FIG. 7, a probing device 700 according to a third embodiment of the invention comprises the same elements as the device in FIG. 4, for which the same references are used, except for the elements to be described hereinafter. As in the second embodiment, the probing device 700 is designed to account for a deviation between an actual position and/or orientation of the box 110, and a desired position and/or orientation on the desired path, in the update of the focusing parameters $P_{F/B}$. On the other hand, unlike the first and second embodiments, the desired path segments $S^{(i)}$ are not directly associated with previously calculated focusing parameters $P_{ref}^{(i)}{}_{F/B}$ but with parameters from an adjustment operation providing, by means of calculation, a value of the focusing parameters on the basis of each position on the desired path. According to this embodiment, it is understood that the precision of the movement of the focal point F in the object 102 is enhanced without having to increase the number of segments $S^{(i)}$ in the parts of the desired path which are not parallel with the desired movement of the focal point F. In particular, in the example in FIG. 8 illustrating the two-dimensional path 302, 306, 304 of the probe of the device 700, a single segment can now cover the oblique part 306 since the correspondence (i.e. the change of reference) between the part 306 and the trajectory ideally followed by the focal point F can be completely determined using an adjustment operation defined by an affine application.

Hereinafter in the description, to simplify the notations, only the two-dimensional coordinates in the plane of the figures will be used, since those skilled in the art could readily adapt the teaching hereinafter to three dimensions. In this way, the focusing parameters $P_{F/B}$, i.e. the successive coordinates of the focal point F in relation to the box 110, may each be represented by a depth P in relation to the box 110 and an angle α representing the orientation of the box 110 in relation to a predetermined direction, for example the vertical direction. As in the previous examples, the desired path comprises linear path segments $S^{(i)}$, for example arranged end to end. In the database 134, focusing data are associated with each segment. In the probing device 700, the focusing data associated with a path segment $S^{(i)}$ comprise parameters from an adjustment operation for calculating a focusing parameter value on the basis of each position on the path segment $S^{(i)}$, particularly parameters from an affine application such as a depth P(i) and an angle α(i). The angle α(i) represents the slope of the segment and is suitable for defining the direction wherein the focal point F is situated in relation to the box 110 and correcting the depth P(i) when the box moves along the segment $S^{(i)}$, as explained hereinafter.

In this way, in the probing device 700 in FIG. 7, the selection instructions 404 are replaced by instructions 702 and 704.

The instructions 702 are designed to select one of the path segments $S^{(i)}$ saved in the database on the basis of the non-adjusted position $P_{B/O}$. Moreover, the instructions 702 are designed to provide focusing data associated with the selected path segment $S^{(i)}$, i.e., in the example described, the depth P(i) and the angle α(i) associated with the selected path segment $S^{(i)}$.

The instructions 704 are designed to calculate, by means of a mathematical adjustment formula, in this instance an affine mathematical application defined by P(i) and α(i), the position $P_{F/B}$ of the focal point F on the basis of the adjusted position $P_{B/O}$ of the box 110 on the selected path segment $S^{(i)}$. In the probing device 700, the formula providing the position $P_{F/B}$ of the focal point F corresponding to a position s on the path $S^{(i)}$ is: $P_{F/B}$=P(i)+s·sin α(i).

In this way, in the probing device 700, the predefined associations comprise the set consisting of the focusing data saved in the database 134 (P(i) and α(i)) a mathematical application in turn defined by the focusing data, these two elements associating focusing parameters with each position of the box on the path thereof.

With reference to FIG. 8, an example of use of the device 700 in FIG. 7 will now be described.

The object 102 comprises a face having, in the plane of FIG. 7, two horizontal parts 302, 304 and one oblique part 306 joining the two horizontal parts 302, 304. The focal point F needs to follow a rectilinear trajectory at a constant depth in the object 102, i.e. at a distance $P_A$ from the horizontal part 302 and at a distance $P_B$ from the horizontal part 304.

The desired path comprises three path segments $S^{(1)}$ ... $S^{(3)}$, defined to each cover the parts 302, 306 and 304, respectively, each associated with respective focusing data {P(1); α(1)} ... {P(3); α(3)} equal to:

{P(1);α(1)}={$P_A$;0},

{P(2);α(2)}={$P_A$;α}, and

{P(3);α(3)}={$P_B$;0}.

In concrete terms, the parameters P(i), α(i) make it possible to change the reference between the desired path defined by the three segments $S^{(1)}$ ... $S^{(3)}$ and the horizontal rectilinear trajectory to be followed by the focal point F.

In this way, the first path segment $S^{(1)}$ covers the first horizontal part 302, parallel and situated at the distance $P_A$ from the focusing trajectory. The instructions 704 calculate the position of the focal point in relation to the box. As the angle α(1) is zero, this means that there is no correction to be made to the depth P(1)=$P_A$ and thus that the focal point remains at a constant depth $P_A$ and moves parallel with the first horizontal part 302.

The next path segment $S^{(2)}$ covers the oblique part 306. The instructions 704 calculate the position of the focal point in relation to the box. As the angle α(2)=α is not zero, at each position s of the box 110 on the segment $S^{(2)}$ the instructions 704 provide the position calculated by means of the formula $P_{F/B}$=P(2)+s·sin α(2)=$P_A$+s·sin α to correct the slope of the part 306. In this way, the focal point F moves in a linear and horizontal fashion in line with the movement thereof in parallel with the first segment $S^{(1)}$.

The third path segment $S^{(3)}$ covers the horizontal part 304, parallel and situated at the distance $P_B$ from the focusing trajectory. The instructions 704 calculate the position of the focal point in relation to the box. As the angle α(3) is zero, this means that there is no correction to be made to the depth P(3)=$P_B$ and thus that the focal point F remains at a constant depth and moves parallel with the horizontal part 304 at the distance $P_B$ therefrom in line with the previous movements thereof.

In this way, by means of the focusing data {P(1); α(1)} ... {P(3); α(3)} actually comprising the reference change parameters associated with the predefined path segments $S^{(1)}$ ... $S^{(3)}$, the focal point F moves in a linear and horizontal fashion when the probe 106 moves along the surface of the object 102, despite the fact that the surface of the object 102 is not a solely horizontal line.

It is noted that, in the example in FIG. 8, the probe 106 indeed moves along the desired path as provided for in the database 134. However, as in the second embodiment and as specified above, the probing device 700 is designed to account for or a deviation between an actual position and/or orientation of the box 110, and a desired position and/or orientation on the desired path, in the update of the focusing parameters $P_{F/B}$. In this way, if the probe 106 deviated as in the part 304 in FIG. 6 in relation to the desired path, this deviation could be measured and calculated using locating means 130 and deviation determination instructions 406, to be subsequently taken into account in the update of the focusing parameters $P_{F/B}$ by the correction instructions 408.

Furthermore and advantageously, the correction parameters used by the correction instructions 408 may be of the same type as the focusing data saved in the database 134 and processed by the instructions 702 and 704. In the example of the third embodiment detailed above, the focusing data are distance P(i) and angle α(i) parameters which are indeed of the same type as the correction parameters $P_{B/B}$ (deviation in position) and $O_{B/B}$ (deviation in orientation) provided by the deviation determination instructions 406 to the correction instructions 408. In this way, the correction made by the correction instructions 408 may merely consist of correcting the focusing data P(i) and α(i) saved in the database 134 using the values $P_{B/B}$ and $O_{B/B}$ measured using the same adjustment formula (affine application) as described above.

The respective contribution of the focusing data (pre-saved in the database 134) and the correction parameters (measured using the locating means 130) in this third embodiment can even be modulated as required, the correction made by the instructions 408 being suitable for compensating for inaccuracies or deficiencies on the pre-saved data. It is thus not necessary to have very precise prior knowledge of the shape of the object 102 since the deviation correction provided in the instructions 408 is made automatically without needing a mechanical correction.

If needed, it would even be possible not to account for the actual non-plane shape of the object 102 at all in the database 134, the desired path in this case being saved as rectilinear and horizontal and always parallel with the trajectory to the followed by the focal point F in the object 102. In this case, with reference to the horizontal part 302, the movement of the probe 106 on the parts 306 and 304 would be considered by the probing device 700 to be a deviation in relation to the desired path (which is in this case a horizontal line extending from the part 302) and would be entirely treated as such by the correction instructions 408 for which the values $P_{B/B}$ and $O_{B/B}$ would fully contribute to the adjustment operation defined by the affine mathematical formula for updating the focusing parameters.

It is clear that an ultrasound probing device such as those described above is suitable for envisaging a focal point trajectory independent from the surface of the object, and thus test complex objects.

Furthermore, it should be noted that the invention is not limited to the embodiments described above.

In particular, the computer program instructions could be replaced by electronic circuits designed to carry out the same functions.

Furthermore, the positions and orientations described above could be expressed indirectly via an external reference frame in relation to the system for example associated with a frame assumed to be fixed. For example, the position $P_{B/O}$ of the box 110 in relation to the object 102 could be expressed by the following two positions: the position of the box 110 in relation to the external reference frame and the position of the object 102 in relation to the external reference frame.

Furthermore, non-linear path segments should be used.

Furthermore, the focusing parameters may be expressed in relation to the box as described above or in relation to the object to be examined. In the latter case, the position of the box in relation to the object is used to locate the position of the focal point in relation to the box.

Furthermore, rather than discrete focusing parameter values associated with path segments, the predefined associations could comprise a continuous function providing the focusing parameter value on the basis of the box position. For example, in the case of FIG. 3, this function could be an affine function defining the positions of the focal point F at increasing depths in the reference of the box and constant depths in the reference of the object, presenting a suitable angle for the oblique part. In this way, the movement of the focal point would remain horizontal on the three parts of the object, particularly along the oblique part.

Finally, it would be obvious for those skilled in the art that various modifications may be made to the embodiments described above, in the light of the teaching disclosed herein. In the claims hereinafter, the terms used should not be interpreted as limiting the claims to the embodiments disclosed in the present description, but should be interpreted to include therein all the equivalents intended to be covered by the claims due to the wording thereof and which can be envisaged by those skilled in the art by applying their general knowledge to the implementation of the teaching disclosed herein.

The invention claimed is:

1. An ultrasound probing device, comprising:
a box;
locating means to provide a position of the box in relation to a reference frame associated with an object to be examined;
means for determining a delay law on the basis of focusing parameters representing a desired position of a focal point in relation to a reference frame associated with the box;
control means to provide control signals on the basis of the delay law;
transducers attached to the box, to receive control signals and, in response, to transmit ultrasonic waves in the object which are delayed with respect to each other according to the delay law such that the ultrasonic waves focus at the focal point defined by the focusing parameters; and
means for updating the focusing parameters based on predefined associations between positions on a desired path of the box in relation to the reference frame associated with the object and the corresponding focusing parameter values and the position of the box.

2. An ultrasound probing device according to claim 1, wherein the means for locating the box comprises a sensor to measure the position of the box.

3. An ultrasound probing device according to claim 1, wherein the updating means comprises selection means to provide a focusing parameter value associated, by the predefined associations, with at least one position on the desired path, on the basis of the position of the box.

4. An ultrasound probing device according to claim 3, wherein the updating means updates the focusing parameters to the focusing parameter value provided by the selection means.

5. An ultrasound probing device according to claim 3, wherein the updating means further comprises:
adjustment means to determine an adjusted position of the box in relation to the reference frame associated with the object on the desired path on the basis of the position of the box and/or an adjusted orientation of the box on a desired orientation of the box on the basis of an orientation of the box;
means for determining deviations to determine a deviation in position between the position of the box and the adjusted position, and/or a deviation in orientation between the orientation of the box and the adjusted orientation;
correction means to correct the focusing parameter value provided by the selection means on the basis of the deviation in position and/or the deviation in orientation, and wherein the updating means updates the focusing parameters to the corrected focusing parameter value provided by the correction means.

6. An ultrasound probing device according to claim 3, wherein:
the desired path comprising path segments, the predefined associations associate reference focusing parameter values respectively with each path segment, the selection means selects one of the path segments on the basis of the position of the box and to provide the reference value associated with the selected path segment.

7. An ultrasound probing device according to claim 3, wherein the predefined associations comprise parameters of an adjustment operation providing a focusing parameter value on the basis of a position on the desired path and the selection means comprises means to calculate, using the adjustment operation parameters, the value of the focusing parameters on the basis of a position on the desired path determined on the basis of the position of the box.

8. An ultrasound probing device according to claim 4, wherein the transducers are attached in a movable manner to the box, comprising means for locating the transducers to determine positions of the transducers in relation to a reference frame associated with the box, and wherein the means for determining the delay law are further configured to determine the delay law on the basis of the positions of the transducers.

9. A method for controlling the transducers of an ultrasound probe, comprising:
receiving a position of a box of the probe in relation to a reference frame associated with an object to be examined, the transducers being attached to the box;
determining a delay law on the basis of focusing parameters, referenced, representing a desired position of a focal point in relation to a reference frame associated with the box;
providing control signals to the transducers on the basis of the delay law; and
updating the focusing parameters, on the basis of predefined associations between positions on a desired path of the box in relation to the reference frame associated with the object and the corresponding focusing parameter values and the position of the box.

10. A non-transitory computer readable medium to be read by a computer and/or executed by a processor, comprising:
instructions for implementation of a method of claim 9 for controlling transducers of an ultrasound probe, when executed by a computer.

* * * * *